United States Patent
Bru Roig et al.

(10) Patent No.: US 10,800,724 B2
(45) Date of Patent: Oct. 13, 2020

(54) PREPARATION OF 14-METHYL-16-OXABICYCLO[10.3.1] PENTADECENES FROM 3-METHYL-1,5-CYCLOPENTADECANE-DIONE

(71) Applicant: BASF SE (REITSTÖTTER, KINZEBACH & PARTNER), Ludwigshafen am Rhein (DE)

(72) Inventors: Miriam Bru Roig, Ludwigshafen am Rhein (DE); Stefan Ruedenauer, Lampertheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/317,279

(22) PCT Filed: Jul. 14, 2017

(86) PCT No.: PCT/EP2017/067811
§ 371 (c)(1),
(2) Date: Jan. 11, 2019

(87) PCT Pub. No.: WO2018/011386
PCT Pub. Date: Jan. 18, 2018

(65) Prior Publication Data
US 2019/0300467 A1   Oct. 3, 2019

(30) Foreign Application Priority Data
Jul. 15, 2016  (EP) ..................................... 16179692

(51) Int. Cl.
*C07C 45/66* (2006.01)
*C07C 45/78* (2006.01)
*C07C 49/587* (2006.01)

(52) U.S. Cl.
CPC .............. *C07C 45/66* (2013.01); *C07C 45/78* (2013.01); *C07C 49/587* (2013.01)

(58) Field of Classification Search
CPC ................................ C07C 45/66; C07C 45/78
See application file for complete search history.

(56) References Cited

U.S. PATENT DOCUMENTS

| | | |
|---|---|---|
| 3,778,483 A | 12/1973 | Becker et al. |
| 4,335,262 A | 6/1982 | Schulte-Elte et al. |
| 2017/0275225 A1 | 9/2017 | Riedel et al. |
| 2017/0283352 A1 | 10/2017 | Fenlon et al. |
| 2017/0292084 A1 | 10/2017 | Stork et al. |
| 2017/0355670 A1 | 12/2017 | Rüdenauer et al. |
| 2018/0002266 A1 | 1/2018 | Bru Roig et al. |
| 2018/0044313 A1 | 2/2018 | Rudenauer et al. |
| 2018/0141888 A1 | 5/2018 | Rüdenauer et al. |
| 2018/0171262 A1 | 6/2018 | Rüdenauer et al. |
| 2018/0179136 A1 | 6/2018 | Bru Roig et al. |
| 2018/0208532 A1 | 7/2018 | Parvulescu et al. |
| 2018/0208533 A1 | 7/2018 | Rüdenauer et al. |
| 2018/0244613 A1 | 8/2018 | Rüdenauer et al. |
| 2018/0273458 A1 | 9/2018 | Strautmann et al. |
| 2018/0346397 A1 | 12/2018 | Bru Roig et al. |
| 2018/0346478 A1 | 12/2018 | Werner et al. |

FOREIGN PATENT DOCUMENTS

| | | |
|---|---|---|
| CH | 513791 A | 10/1971 |
| CH | 519454 A | 2/1972 |
| DE | 2916418 A1 | 11/1980 |
| EP | 3199514 A1 | 8/2017 |
| GB | 1205047 A | 9/1970 |

OTHER PUBLICATIONS

Blomquist, A., et al., "Many-membered Carbon Rings. XI. Civetone Homologs", Journal of the American Chemical Society, vol. 77, (1955), pp. 5423-5424.

Inhoffen, H., et al., "Untersuchungen an hochsubstituierten Äthylenen und Glykolen, VIII. Tetrasubstituierte Äthane", Liebigs Annalen der Chemie, vol. 714, No. 1, (1968), pp. 43-56 (in German).

International Search Report for PCT/EP2017/067811 dated Sep. 20, 2017.

Nazir, M., et al., "Partial Reduction of Diketones", Synthesis 1977, vol. 7, (1977), p. 466.

Written Opinion of the International Searching Authority for PCT/EP2017/067811 dated Sep. 20, 2017.

*Primary Examiner* — Sikarl A Witherspoon
(74) *Attorney, Agent, or Firm* — Faegre Drinker Biddle & Reath LLP

(57) ABSTRACT

The present invention relates to a method for preparing 14-methyl-16-oxabicyclo-[10.3.1]pentadecenes in a two-step synthesis from 3-methyl-1,5-cyclopentadecane-dione as starting material.

18 Claims, No Drawings

PREPARATION OF 14-METHYL-16-OXABICYCLO[10.3.1] PENTADECENES FROM 3-METHYL-1,5-CYCLOPENTADECANEDIONE

CROSS-REFERENCE TO RELATED APPLICATIONS

This application is a national stage application (under 35 U.S.C. § 371) of PCT/EP2017/067811, filed Jul. 14, 2017, which claims benefit of European Application No. 16179692.5, filed Jul. 15, 2016, both of which are incorporated herein by reference in their entirety.

BACKGROUND OF THE INVENTION

The present invention relates to a method for preparing 14-methyl-16-oxabicyclo-[10.3.1]pentadecenes in a two-step synthesis from 3-methyl-1,5-cyclopentadecane-dione as starting material.

STATE OF THE ART

Saturated macrocyclic ketones having 14- to 18-membered rings, e.g. muscone (3-methylcyclopentadecanone), have interesting properties as fragrances or flavors. 3-methyl-cyclopentadec-4-en-1-one and 3-methyl-cyclopentadec-5-en-1-one are two unsaturated homologues of muscone that are also valuable musk-like aroma chemicals. Both double bond isomers and the mixtures thereof are also denoted as "muscenone" (DH-muscone). Formula (A) depicts muscenone without consideration of possible position and configuration isomers:

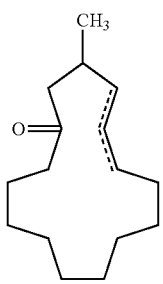

(A)

wherein one of the symbols ═══ is a single bond and the other is a double bond.

The preparation of Muscenone has been known for a long time. U.S. Pat. No. 3,778,483 describes methods for the preparation of macrocyclic compounds, in particular cyclopentadecanone (Exaltone®) and 3-Methylcyclopentadecane-1-one (muscone). It is inter alia disclosed that a partial reduction of the diketone (B) can be carried out by catalytic hydrogenation with Raney nickel at room temperature. Example 7 of this document describes the hydrogenation of diketone (B) to yield cyclopentadecan-5-ol-1-one (C) in a predominant proportion. The crude cyclopentadecan-5-ol-1-one (C) is subjected to a reaction with benzenesulfonic acid in toluene to obtain a mixture of 3-methyl-cyclopentadec-4-en-1-one and 3-methyl-cyclopentadec-5-en-1-one (A)

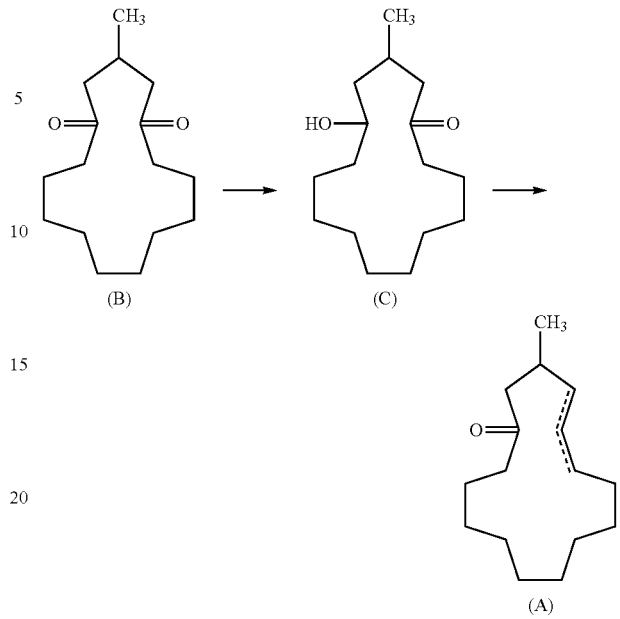

U.S. Pat. No. 4,335,262 describes inter alia the preparation of muscenone (A) via dehydrogenation and dehydration of the cyclic diol (D) with Raney copper to obtain the unsaturated cyclic ether (E) which is afterwards subjected to a reaction with phosphoric acid in toluene to yield (A)

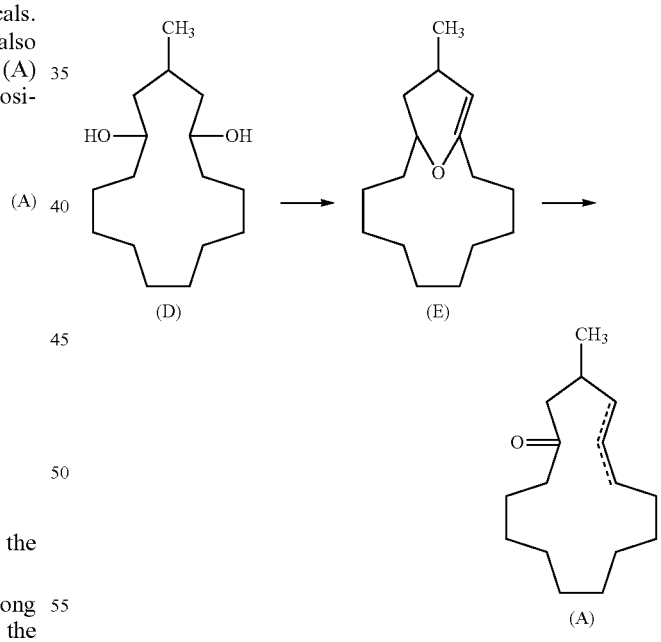

The afore-mentioned routes still need improvement as the complete reduction of the diketone employed as starting material to the corresponding diol occurs as undesirable side reaction.

A. T. Blomquist and J. Wolinsky describe in J. Am. Chem. Soc. 77, 1955, p. 5423-5424 the partial reduction of 1,9-cyclohexadecanedione and 1,10-cyclooctadecane-dione using Adams catalyst in acetic acid. However, apart from the hydroxyketones also the corresponding diols were obtained and had to be separated from the reaction mixture.

H. H. Inhoffen et al. describe in Liebigs Ann. Chem. 714, 1968, p. 43-56 the partial reduction of diketones of the general formula (F) to yield the corresponding hydroxyketones (G). Again, the corresponding diols were obtained as side products and had to be separated by chromatography. The yield of the hydroxyketones was 40 to 45%.

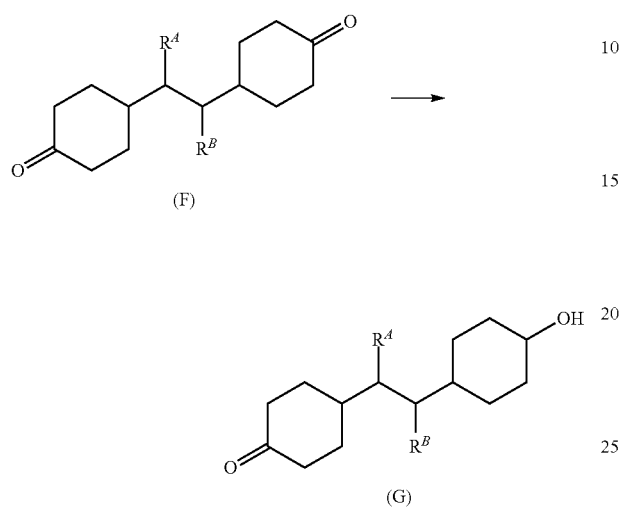

A suitable technique to achieve partial reduction of diketones is to protect one of the carbonyl functions and subject the resulting monoketone to the reduction (Synthesis, 7, 1977. p. 466). The disadvantage of such protection and deprotection sequences is the high complexity of the synthesis.

It is an object of the present invention to provide an improved method for preparing muscenone that avoids the disadvantages of the afore-mentioned known processes.

It has now been found, surprisingly, that the reduction leads to a mixture of two partially reduced products (3-methyl-cyclopentadecan-5-ol-1-one and 14-methyl-16-oxabicyclo[10.3.1]pentadec-1(15)-ene) that both together can be subjected to a following reaction step to muscenone.

It has further been found that the reduction of 3-methyl-1,5-cyclopentadecane-dione with $NaBH_4$ allows a simple control of the reaction to obtain a high selectivity with regard to the two partially reduced products. The amount of 3-methyl-cyclopentadecane-1,5-diol which is the undesirable product obtained by the complete reduction of both keto groups of 3-methyl-1,5-cyclopentadecanedione can be kept remarkably low. The main components of the reaction mixture are the two partially reduced products and the diketone starting material. It has further been found that the latter is inert in the second reaction step and can be easily separated off from the muscenone product and can be recycled to the first reaction step. In other words, the process of the invention allows a partially reduction with high selectivity towards products that can be converted to muscenone, wherein the major amount of the rest of the reaction mixture can be recycled.

SUMMARY OF THE INVENTION

The present invention relates to a process for preparing at least one compound of the general formula (I)

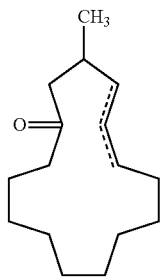

wherein one of the symbols ----- is a single bond and the other is a double bond,
which comprises
a) providing a starting material comprising the compound of the general formula (II)

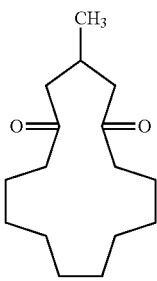

and reacting the starting material with $NaBH_4$ to yield a reaction product comprising a mixture of the compounds of the general formulae (IIIa) and (IIIb)

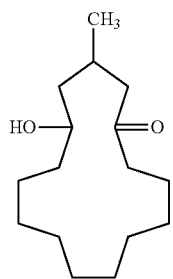

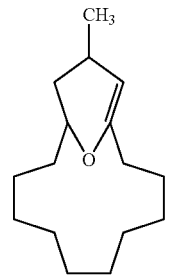

and where the $NaBH_4$ is employed in an amount of 0.07 to 0.7 mole equivalents, based on the amount of the compound of the general formula (II);
b) treating the reaction product obtained in step a) with an acid to yield at least one compound of the general formula (I).

A specific embodiment is a method in which the NaBH$_4$ is employed in an amount of 0.1 to 0.5 mole equivalents, based on the amount of the compound of the general formula (II). If the application quantity of the NaBH$_4$ is in the mentioned range, the reaction mixture obtained in step a) has an advantageous content, i.e. a high amount of the compounds (IIIa) and (IIIb) and a low amount of 3-methyl-cyclopentadecan-1,5-diol.

DESCRIPTION OF THE INVENTION

The method according to the invention has the following advantages:
- Using the method according to the invention, it is possible to synthesize muscenone in two reaction steps starting from 3-methyl-1,5-cyclopentadecane-dione.
- The process of the invention avoids the use of hydrogen which affords complex and expensive technology.
- The oxidation of 3-methyl-1,5-cyclopentadecanedione (II) with NaBH$_4$ in the first reaction step leads to a mixture comprising 3-methyl-cyclopentadecan-5-ol-1-one (IIIa) and 14-methyl-16-oxabicyclo[10.3.1]pentadec-1(15)-ene (IIIb), i.e. two partially oxidized products that both together can be transformed to muscenone in a single reaction step. It is not necessary to separate compounds (IIIa) and (IIIb).
- It is possible to control the reaction in step a) to obtain a high selectivity with regard to the mixture of compounds (IIIa) and (IIIb). This is possible by choosing an appropriate amount of NaBH$_4$ and/or by choosing an appropriate reaction temperature and/or by terminating the reaction before complete conversion of the diketone (II). An over-reduction can be essentially avoided so that the amount of the undesirable 3-methyl-cyclopentadecane-1,5-diol (IV) can be kept remarkably low.
- The main components of the reaction mixture obtained in step a) are the two partially oxidized products (IIIa) and (IIIb) and the diketone starting material (II). It has been found that (II) is inert under the condition of reaction step b) and can be easily separated off from the muscenone product (I) and can be recycled to the first reaction step a).

Unless otherwise specified in more detail below, the term "muscenone" and the formula (I) refers to all possible position and configuration isomers in pure form and any mixture thereof. In particular, the term "muscenone" and the formula (I) refers to 3-methylcyclopentadec-4-en-1-one, 3-methylcyclopentadec-5-en-1-one and any mixture thereof. Further, it refers to E/Z-mixtures of any composition and also the pure conformational isomers. Further, it also refers to all enantiomers in pure form and also racemic and optically active mixtures of the enantiomers of these compounds.

For the purposes of illustration only, the isomers of 3-methylcyclopentadec-5-en-1-one are:
(−)-(3R,5Z)-3-methylcyclopentadec-5-en-1-one,
(+)-(3S,5Z)-3-methylcyclopentadec-5-en-1-one,
(−)-(3R,5E)-3-methylcyclopentadec-5-en-1-one and
(+)-(3S,5E)-3-methylcyclopentadec-5-en-1-one.

All muscenone compositions are valuable aroma chemicals and can in particular be used to confer, improve, enhance or modify the odor properties of a perfuming composition or a perfumed article. Due to the actual composition the olfactoric properties may vary e.g. from a strong and pure smell of musk to more woody notes.

Step a)

The synthesis of 3-methyl-1,5-cyclopentadecanedione (II) that is employed as starting materials in step a) of the process according to the invention can be performed in analogy to the methods for the synthesis of 1,5-cyclopentadecanedione described in CH 519454 and CH 513791. In principle, 14-methyl-bicyclo[10.3.0]pentadec-1(12)-en (V)

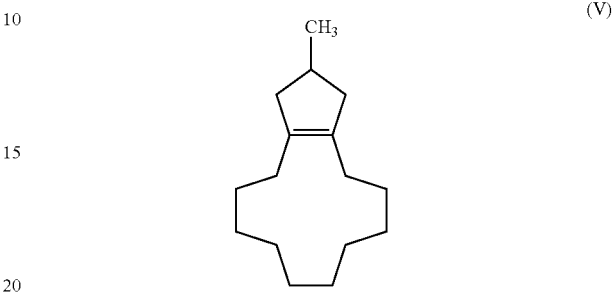

is subjected to an oxidation with a suitable oxidation agent. Suitable oxidation agents are e.g. KMnO$_4$, O$_3$, H$_2$O$_2$ and Pb$_3$O$_4$.

A method for the preparation of 14-Methyl-bicyclo[10.3.0]pentadec-1(12)-en (V) is described inter alia in DE-A-29 16 418.

In reaction step a) the NaBH$_4$ is employed in an amount of 0.07 to 0.7 mole equivalents, preferably 0.1 to 0.5 mole equivalents, based on the amount of the compound of the general formula (II).

In a suitable embodiment of step a), the NaBH$_4$ is added to the compound of the general formula (II). For the addition, the compound of the general formula (II) is preferably employed as a solution in a solvent. Suitable solvents are mentioned in the following. The NaBH$_4$ can be added to the compound of the general formula (II) in form of a solid or a solution in a solvent. Preferably, if the NaBH$_4$ is employed as a solution the solvent used for dissolving the compound of the general formula (II) and the solvent of the NaBH$_4$ are the same.

The addition of the NaBH$_4$ to compound of the general formula (II) can be carried out in a single addition step or in portions. Preferred is the addition in portions.

Preferably, the reaction in step a) is effected in the presence of a solvent, selected from alcohols, ethers, water and mixtures thereof.

More preferably, the solvent is selected from C$_1$-C$_4$-alkanols, C$_1$-C$_4$-alkylene glycols, mono- and di-(C$_1$-C$_4$-alkyl) ethers of C$_1$-C$_4$-alkylene glycols, polyalkylene glycols, polyalkylene glycol mono- and di-(C$_1$-C$_4$-alkyl) ethers, water and mixtures thereof.

The solvent is particularly preferably selected from among methanol, ethanol, ethylene glycol, ethylene glycol dimethyl ether, mixtures thereof and mixtures of the aforementioned solvents with water.

In particular, methanol or ethanol is used as solvent.

In a preferred embodiment the reaction in step a) is effected in the presence of an added acid. Suitable acids are selected from acids having a pK$_a$ value in the range of from 1 to 7, preferably of from 2 to 6. For polyprotic acids the pK$_a$ value for dissociation of the first proton (pK$_{a1}$) is preferably in the range of from 1 to 7, preferably of from 2 to 6. Suitable acids are also weakly acidic cation exchanger.

A specially preferred acid is benzoic acid.

In a further preferred embodiment the reaction in step a) is effected without the addition of an acid.

Preferably, the reaction in step a) is effected at a temperature in the range of from −10 to 25° C., more preferably from −5 to 15° C., in particular from 0 to 10° C. In a suitable embodiment, the reaction in step b) comprises a first period, wherein the NaBH$_4$ is added at a first temperature and a second period after the addition of NaBH$_4$ is completed at a second temperature. Preferably, the first temperature is in a range of from −10 to 25° C., more preferably from 0 to 20° C. Preferably, the second temperature is in a range of from 0 to 50° C., more preferably from 10 to 35° C. In particular, the first temperature is always lower than the second temperature.

Preferably, the reaction in step a) is effected at a pressure within a range from 500 mbar to 10 bar, more preferably 900 mbar to 3 bar, especially at ambient pressure.

The reaction in step a) can be carried out in a batch, semi-batch or continuous process.

In order to control the reaction in step a) the content of at least one of the components (II), (IIIa), (IIIb) or (IV) in the reaction zone or in a discharge from the reaction zone can be determined by suitable analytical measures. In a batch process or semi-batch process, samples can be taken from the reaction zone at regular intervals and the content of at least one of the components (II), (IIIa), (IIIb) or (IV) detected. In a continuous process this measurement can also be carried out by means of an on-line measurement device in the discharge from the reaction zone. The content of at least one of the components (II), (IIIa), (IIIb) or (IV) can be determined, for example, by gas chromatography (GC), infrared spectroscopy, UV spectroscopy or chemiluminescence analysis. In a special embodiment, the quantitative analysis is performed by gas chromatography.

Quantitative GC analysis is a standard method known to a person skilled in the art. In principle, in GC chromatography (as generally in column chromatography) the area of a peak is usually proportional to the number of moles of the corresponding compound. In a mixture of more than one analyte the area of each peak corresponds to the mole fraction of a particular compound in the mixture. The use of an internal standard serves to compensate errors and get a high analytical precision. Precise estimation of the peak areas and calculation of the corresponding mole fractions can be performed with the electronic integration unit of the chromatograph.

The conversion with regard to starting component (II) in % at a reaction time t is defined as:

$$\text{conversion } [\%] = \frac{\text{initial amount of } (II) - \text{amount of } (II) \text{ at } t}{\text{initial amount of } (II)} \cdot 100$$

In a preferred embodiment of the invention in step a) the conversion with regard to compound (II) is in a range of from 10 to 80%, preferably of from 20 to 75%. When the desired conversion is reached, the reaction can be terminated, e.g. by adding a substance that deactivates the NaBH$_4$. Suitable substances that deactivate NaBH$_4$ are mentioned in the following.

The total amount of components (IIIa) and (IIIb) in the reaction product obtained in step a) is preferably at least 20 mol %, more preferably at least 30 mol %, in particular at least 40 mol %, based on the total amount of components (II), (IIIa), (IIIb) and (IV) in the reaction product.

The amount of 3-methyl-cyclopentadecan-1,5-diol (IV) in the reaction product obtained in step a) is preferably not more than 20 mol %, more preferably not more than 15 mol %, based on the total amount of components (II), (IIIa), (IIIb) and (IV) in the reaction product.

The reaction product obtained in step a) can be subjected to a work-up prior to its use in reaction step b). Preferably, the reaction product obtained in step a) is subjected to at least one after-treatment step, selected from
  deactivation of unreacted NaBH$_4$,
  removal of at least one component selected from solvent, acid employed for the reaction and/or the deactivation of unreacted NaBH$_4$, salts obtained in the deactivation of unreacted NaBH$_4$.

Unreacted NaBH$_4$ can be deactivated by addition of an acid. Suitable acids are e.g. HCl, H$_2$SO$_4$, HNO$_3$, H$_3$PO$_4$, etc. If the unreacted NaBH$_4$ shall be deactivated this is performed preferably prior to any purification step. Thus, the reaction products formed in the deactivation of NaBH$_4$ can be at least partly removed in the following purification.

In a suitable embodiment, the reaction product obtained in step a) can be subjected to a purification by extraction. For the extraction a solvent mixture is employed that comprises two at least partly immiscible solvents that form two liquid phases. Preferably, water and organic solvents that are already present in the reaction product of step a) are not removed prior to the extraction. For the extraction one at least partly water immiscible organic solvent is added to the reaction product obtained in step a).

Suitable at least partly water immiscible organic solvents are halogenated hydrocarbons, aliphatic ethers, alkylester of aliphatic carbon acids, etc. Preferred at least partly water immiscible organic solvents are dichloromethane chloroform, acetyl acetate, diethyl ether, etc. If the reaction product obtained in step a) does not already contain a sufficient amount of water and/or an essentially water-miscible solvent, then additional water and/or an essentially water-miscible solvents are added to the reaction product obtained in step a). The two liquid phases are brought into intimate contact, separated, the water phase is separated off and the organic phase containing components (IIIa) and (IIIb) and optionally (II) and/or (IV) is collected. The extraction may be repeated once or several times. The combined organic phases may be subjected to at least one washing step. Suitable washing media are e.g. water or brine. From the optionally washed organic phase the organic solvent can be removed, preferably by evaporation.

Step b)

In step b) of the method according to the invention, the reaction product obtained in step a) is treated with an acid to yield at least one compound of the general formula (I).

In principle, any acid can be used for the reaction in step b), i.e. any substance having Brönstedt or Lewis acidity. Examples of suitable catalysts are protic acids, such as hydrochloric acid, sulfuric acid, phosphoric acid, methanesulfonic acid and p-toluenesulfonic acid, acidic molecular elemental compounds, such as aluminum chloride, boron trifluoride, zinc chloride, oxidic acidic solids, such as zeolites, silicates, aluminates, aluminosilicates, clays and acidic ion exchangers.

In a preferred embodiment the acid employed in reaction step b) comprises or consists of phosphoric acid.

Preferably, the reaction in step b) is effected in the presence of a solvent having a boiling point at 1013.25 hPa of at least 85° C.

Preferably, the reaction in step b) is effected at a pressure within a range from 500 mbar to 10 bar, more preferably 900 mbar to 3 bar, especially at ambient pressure.

In a preferred embodiment the reaction in step b) is effected in the presence of a solvent selected from hydrocarbons and hydrocarbon mixtures, in particular selected from toluene, xylene, heavy naphtha, petroleum ether, decalin and mixtures thereof. A preferred solvent is toluene.

The reaction product obtained in step b) can be subjected to a work-up prior to the use as aroma chemical.

In a special embodiment the reaction product obtained in step b) is subjected to a separation to obtain at least one fraction (F-I) enriched in the compound of the general formula (I) and a fraction (F-II) enriched in the unreacted compound of the formula (II).

The reaction product obtained in step b) is preferably subjected to a distillative separation. Suitable apparatuses for distillative separation comprise distillation columns, such as tray columns which may be equipped with bubble-caps, sieve plates, sieve trays, structured packings, random packings, valves, side draws, etc., evaporators, such as thin film evaporators, falling film evaporators, forced circulation evaporators, Sambay evaporators, etc., and combinations thereof. The reaction product obtained in step b) is preferably subjected in step e) to a distillative separation in at least one distillation column which is provided with separating internals.

A fraction (F-I) enriched in the compound of the general formula (I) is preferably isolated from the reaction product obtained in step b) which fraction has a content of 3-methyl-cyclopentadecane-1,5-diol (IV) of at most 2% by weight, particularly preferably at most 1% by weight, particularly preferably at most 0.1% by weight.

A fraction (F-I) enriched in the compound of the general formula (I) is preferably isolated from the reaction product obtained in step b) which fraction has a content of the compound (I) of at least 90% by weight, particularly preferably at least 95% by weight, particularly preferably at least 99% by weight.

The fraction (F-II) enriched in the compound of the formula (II) is preferably recycled to the reaction in step a).

The compositions obtainable by the method according to the invention are particularly suitable as fragrances or for providing a fragrance.

The compositions according to the invention for use as fragrances can be diluted, as desired, with at least one customary solvent in this area of application. Examples of suitable solvents are: ethanol, dipropylene glycol or ethers thereof, phthalates, propylene glycols, or carbonates of diols, preferably ethanol. Water is also suitable as solvent for diluting the fragrance compositions according to the invention and can advantageously be used together with suitable emulsifiers.

The fragrances on the basis of the compounds (I) obtainable by the method according to the invention have high stability and durability. The compounds of the formula (I) obtainable by the method according to the invention either in pure form or mixtures thereof are characterized by a pleasant odor of musk.

The fragrances obtained by the method according to the invention are suitable for incorporation in cosmetic compositions and also utility and consumer goods or agents, such as are described in more detail below, in which the fragrance may be incorporated in the goods mentioned or also may be applied to such goods. Here, for the purposes of the overall present invention, an organoleptically effective amount is to be understood as meaning particularly an amount which suffices, when used as intended, to bring about a scent impression for the user or consumer.

Suitable cosmetic compositions are all customary cosmetic compositions. The compositions in question are preferably perfume, Eau de Toilette, deodorants, soap, shower gel, bathing gel, creams, lotions, sunscreen, compositions for cleansing and care of hair, such as shampoo, conditioner, hair gel, hair setting compositions in the form of liquids or foams and other cleansing or care compositions for the hair, compositions for decorative application on the human body, such as cosmetic sticks, for example lipsticks, lip care sticks, concealing sticks (concealers), blushers, eye shadow pencils, lip liner pencils, eyeliner pencils, eyebrow pencils, correction pencils, sunscreen sticks, antiacne sticks and comparable products, and also nail varnishes and other products for nail care.

The fragrances obtained by the method according to the invention are specifically suitable for use in perfumes, e.g. as Eau de Toilette, shower gels, bathing gels and body deodorants.

They are also suitable for aromatizing consumer or utility goods into which they are incorporated or onto which they are applied and to which they thereby impart a pleasant fresh green accent. Examples of consumer or utility goods are: room air deodorants (air care), cleaning compositions or care compositions for textiles (specifically detergents, fabric softeners), textile treatment compositions, such as ironing aids, scouring agents, cleaning compositions, care compositions for treating surfaces, for example furniture, floors, kitchen appliances, glass panes and windows and also monitors, bleaches, toilet blocks, limescale removers, fertilizers, construction materials, mold removers, disinfectants, products for the car and vehicle care and the like.

The examples which follow serve to illustrate the invention, but without restricting it in any way.

EXAMPLES

Gas chromatographic analyses (GC) were carried out in accordance with the following method:

GC-system: Agilent 7890 Series A;

GC-Column: DB-WAX (30 m (Length), 0.32 mm (ID), 0.25 μm (Film));

Injector at 230° C., detector at 280° C. and flow 1.5 ml.

Temperature program: 80° C. to 250° C. in 3° C./min, 250° C. for 15 min.

Retention times: 3-methyl-1,5-cyclopentadecanedione (II) $t_R$=42.9 min muscenone (I), 4 isomers $t_R$=32.4, 32.8, 33.2, 34.1 min mixture of (III.a) and (III.b) $t_R$=25.2, 44.6 min 3-methyl-1,5-cyclopentadecanediol $t_R$=54.1 min Concentrations of the starting materials and the resulting products were determined by GC analysis. Quantitative analysis was performed by integration of the area under the peaks of the educt, products and the internal standard (diethylenglycol diethyl ether) using the software of the chromatograph.

The conversion is defined as the difference of the area % value of the diketone (II) and 100%.

The selectivity is defined as $$\text{selectivity} = \frac{\text{area \% }((IIIa) + (IIIb))}{\text{conversion}} \cdot 100$$

Example 1 (Comparative)

1 equivalents NaBH$_4$, room temperature

TABLE 1

| amount | mol | equivalents | component |
|---|---|---|---|
| 5 g | 0.020 | 1 | 3-methyl-1,5-cyclopentadecanedione (II) |
| 0.6 g | 0.010 | 1 | NaBH$_4$ |
| 100 mL | | | EtOH |

The diketone (II) and the EtOH are mixed at room temperature. The NaBH$_4$ is added at room temperature in portions. The reaction mixture is stirred at room temperature for 6 h. A sample is taken every hour and further analyzed by GC (see table 2).

| time | diketone [area %] | (III.a) + (IIIb) [area %] | diol [area %] | Conversion (%) | Selectivity (%) |
|---|---|---|---|---|---|
| 0 | 100.00 | | | 0.00 | |
| 1 h | 11.52 | 39.23 | 33.55 | 88.48 | 44.3 |
| 2 h | 7.11 | 36.84 | 39.31 | 92.89 | 39.7 |
| 3 h | 3.01 | 31.6 | 49.73 | 96.99 | 32.6 |
| 4 h | 1.99 | 27.39 | 53.34 | 98.01 | 27.9 |
| 5 h | 1.27 | 24.63 | 58.43 | 98.73 | 24.9 |
| 6 h | 0.62 | 22.64 | 61.68 | 99.38 | 22.8 |

Example 2

0.5 equivalents NaBH$_4$, temperature: 0° C.

TABLE 3

| amount | mol | equivalents | component |
|---|---|---|---|
| 5 g | 0.020 | 1 | 3-methyl-1,5-cyclopentadecanedione (II) |
| 0.37 g | 0.01 | 0.5 | NaBH$_4$ |
| 100 mL | | | EtOH |

The diketone (II) and the EtOH are mixed at room temperature. The NaBH$_4$ is added at 0° C. in portions. The reaction mixture is stirred at 0° C. for 6 h. A sample is taken every hour and further analyzed by GC (see table 4).

TABLE 4

| Time | diketone (II) [area %] | (III.a) + (IIIb) [area %] | diol [area %] | Conversion [%] | Selectivity [%] |
|---|---|---|---|---|---|
| 0 | 100.00 | 0 | 0 | 0.00 | |
| 1 h | 78.16 | 15.68 | 0 | 21.84 | 71.8 |
| 2 h | 69.50 | 20.61 | 3.15 | 30.50 | 67.6 |
| 3 h | 61.86 | 25.63 | 5.54 | 38.14 | 67.2 |
| 4 h | 51.34 | 34.29 | 7.53 | 48.66 | 70.5 |

Example 3

0.25 equivalents NaBH$_4$, RT

TABLE 5

| amount | mol | equivalents | Component |
|---|---|---|---|
| 5 g | 0.020 | 1 | 3-methyl-1,5-cyclopentadecanedione (II) |
| 0.185 g | 0.005 | 0.25 | NaBH$_4$ |
| 100 mL | | | EtOH |

The diketone (II) and the EtOH are mixed at room temperature. The NaBH$_4$ is added at RT in portions. The reaction mixture is stirred at room temperature for 6 h. A sample is taken every hour and further analyzed by GC (see table 6).

After 6 h the reaction is terminated by adding a 5% solution of HCl. After the addition of 50 mL of water the product is extracted with 100 mL of dichloromethane. The organic phase is further washed with 50 mL of a saturated solution of NaHCO$_3$. The organic phase is collected, dried with sodium sulfate and the solvent is evaporated.

TABLE 6

| Time | diketone (II) [area %] | (III.a) + (IIIb) [area %] | diol [area %] | Conversion [%] | Selectivity [%] |
|---|---|---|---|---|---|
| 0 | 100.00 | 0 | 0 | 0.00 | |
| 1 h | 71.81 | 20.36 | 1.55 | 28.19 | 72.2 |
| 2 h | 56.61 | 33.43 | 3.69 | 43.39 | 77.0 |
| 3 h | 49.23 | 39.89 | 4.48 | 50.77 | 78.6 |
| 4 h | 44.80 | 43.58 | 5.08 | 55.20 | 78.9 |
| 5 h | 42.63 | 45.63 | 4.95 | 57.37 | 79.5 |
| 6 h | 40.29 | 47.66 | 5.18 | 59.71 | 79.8 |

Example 4

Synthesis of Muscenone (I)

TABLE 7

| amount | Mol | equivalents | component |
|---|---|---|---|
| 20 g | 0.0657 | 1 | 3-methyl-1,5-cyclopentadecanedione (II) |
| 0.63 g | 0.0164 | 0.25 | NaBH$_4$ |
| 400 mL | | | EtOH |

The diketone (II) and the EtOH are mixed at room temperature. The NaBH$_4$ is added at 5° C. in portions. The reaction mixture is stirred at room temperature for 3 h. After 3 h a sample is taken and analyzed by GC (see table 8).

After 3 h the reaction is terminated by adding a 5% solution of HCl. After the addition of 50 mL of water the product is extracted with 100 mL of dichloromethane. The organic phase is further washed with 50 mL of a saturated solution of NaHCO$_3$. The organic phase is collected, dried with sodium sulfate and the solvent is evaporated. 20.8 g product are obtained.

TABLE 8

| Time | diketone (II) [area %] | (III.a) + (IIIb) [area %] | diol [area %] | Conversion [%] | Selectivity [%] |
|---|---|---|---|---|---|
| 0 h | 94.71 | 0 | 0 | 0.00 | |
| 3 h worked-up | 59.95 | 20.25 | 10.75 | 34.76 | 58.3 |

TABLE 9

| amount | Mol | equivalents | Component |
|---|---|---|---|
| 20.8 g | 0.0174 | 1 | (IIIa) + (IIIb) |
| 1.7 g | 0.0139 | 0.8 | phosphoric acid (80% in water) |
| 100 mL | | | Toluene |

The starting materials are mixed at room temperature and the reaction mixture is heated under reflux for 4.5 h. After cooling the reaction mixture the organic phase is washed twice with 10 mL water, afterwards the organic phase is dried with sodium sulfate. The solvent is then evaporated and 17.8 g product are obtained.

| time | diketone (II) [area %] | (III.a) + (IIIb) [area %] | product (I) [area %] |
|---|---|---|---|
| 0 h | 59.95 | 20.25 | |
| 4.5 h | 43.43 | 0.8 | 33.22 |

This represents a yield of compound (I) from 3-methyl-1,5-cyclopentadecanedione (II) after two steps of 32%. The yield can be increased to 50% if the unreacted 3-methyl-1,5-cyclopentadecanedione (II) is recovered and recycled.

The invention claimed is:

1. A process for preparing at least one compound of the general formula (I)

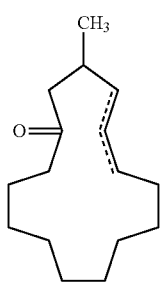

(I)

wherein one of the symbols ===== is a single bond and the other is a double bond, which comprises a) providing a starting material comprising the compound of the general formula (II)

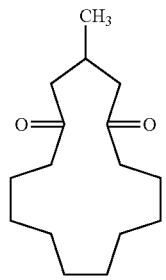

(II)

and reacting the starting material with NaBH$_4$ to yield a reaction product comprising a mixture of the compounds of the general formulae (IIIa) and (IIIb)

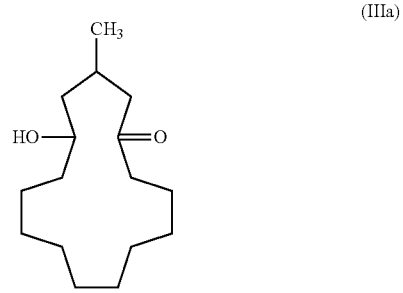

(IIIa)

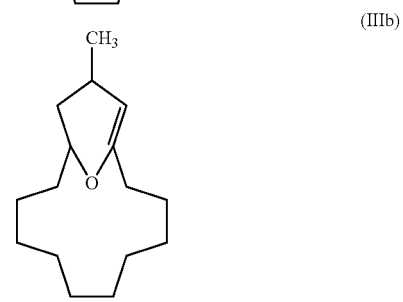

(IIIb)

and where the NaBH$_4$ is employed in an amount of 0.07 to 0.7 mole equivalents, based on the amount of the compound of the general formula (II);

b) treating the reaction product obtained in step a) with an acid to yield at least one compound of the general formula (I).

2. The process according to claim 1, where in reaction step a) the NaBH$_4$ is employed in an amount of 0.1 to 0.5 mole equivalents, based on the amount of the compound of the general formula (II).

3. The process according to claim 1, in which the reaction in step a) is effected in the presence of a solvent.

4. The process according to claim 1, in which the reaction in step a) is effected in the presence of an acid having a pK$_a$ value in the range of from 1 to 7 or a weakly acidic cation exchanger.

5. The process according to claim 1, in which the reaction in step a) is effected in the presence of benzoic acid.

6. The process according to claim 1, wherein the reaction in step a) is effected at a temperature in the range of from −10 to 25° C.

7. The process according to claim 1, wherein in step a) the conversion with regard to compound (II) is in a range of from 10 to 80%.

8. The process according to claim 1, where the reaction product obtained in step a) is subjected to at least one after-treatment step, selected from the group consisting of
deactivation of unreacted $NaBH_4$, and
removal of at least one component selected from solvent, acid employed for the reaction and/or the deactivation of unreacted $NaBH_4$, salts obtained in the deactivation of unreacted $NaBH_4$.

9. The process according to claim 1, wherein the acid employed in reaction step b) comprises phosphoric acid.

10. The process according to claim 1, wherein the reaction in step b) is effected in the presence of a solvent having a boiling point at 1013.25 hPa of at least 85° C.

11. The process according to claim 1, wherein the reaction in step b) is effected in the presence of a solvent selected from the group consisting of hydrocarbons and hydrocarbon mixtures.

12. The process according to claim 1, wherein the reaction product obtained in step b) is subjected to a separation to obtain at least one fraction (F-I) enriched in the compound of the general formula (I) and a fraction (F-II) enriched in the unreacted compound of the formula (II).

13. The process according to claim 12, wherein the fraction (F-II) enriched in the compound of the formula (II) is recycled to the reaction in step a).

14. The process according to claim 1, in which the reaction in step a) is effected in the presence of a solvent selected from the group consisting of alcohols, ethers, water and mixtures thereof.

15. The process according to claim 1, wherein the reaction in step a) is effected at a temperature in the range of from −5 to 15° C.

16. The process according to claim 1, wherein the reaction in step a) is effected at a temperature in the range of from 0 to 10° C.

17. The process according to claim 1, wherein in step a) the conversion with regard to compound (II) is in a range of from 20 to 75%.

18. The process according to claim 1, wherein the reaction in step b) is effected in the presence of a solvent selected from the group consisting of toluene, xylene, heavy naphtha, petroleum ether, decalin and mixtures thereof.

* * * * *